United States Patent
Aramata et al.

(10) Patent No.: US 6,901,975 B2
(45) Date of Patent: Jun. 7, 2005

(54) DRUG SOLUTION CONTAINER WITH A CONNECTOR FOR COMMUNICATING

(75) Inventors: Masafumi Aramata, Osaka (JP); Hideki Yagi, Osaka (JP); Toshikazu Hirayama, Osaka (JP); Satoru Igarashi, Osaka (JP); Yoshihisa Murai, Osaka (JP); Teruhisa Hirobe, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 10/608,547

(22) Filed: Jun. 30, 2003

(65) Prior Publication Data

US 2004/0039365 A1 Feb. 26, 2004

(30) Foreign Application Priority Data

| | | |
|---|---|---|
| Jul. 2, 2002 | (JP) | 2002-193686 |
| Apr. 3, 2003 | (JP) | 2003-099935 |

(51) Int. Cl.[7] ............................................. B65B 1/04
(52) U.S. Cl. ...................... 141/319; 141/329; 141/383; 141/386; 604/414
(58) Field of Search .................... 141/311 R, 312, 141/319, 329, 330, 363–366, 383, 384, 386; 604/411–415

(56) References Cited

U.S. PATENT DOCUMENTS

| | | |
|---|---|---|
| 4,128,098 A | 12/1978 | Bloom et al. |
| 5,211,638 A | 5/1993 | Dudar et al. |
| 5,584,819 A | 12/1996 | Kopfer |
| 5,893,397 A * | 4/1999 | Peterson et al. ............... 141/27 |
| 6,551,299 B2 | 4/2003 | Miyoshi et al. |
| 6,684,918 B1 * | 2/2004 | Thilly et al. .................. 141/25 |
| 6,699,229 B2 * | 3/2004 | Zinger et al. ............... 604/410 |

FOREIGN PATENT DOCUMENTS

| | | |
|---|---|---|
| DK | DE 38 20 204 A1 | 12/1989 |
| EP | 0 499 481 A1 | 8/1992 |
| EP | 0 692 235 A1 | 1/1996 |
| EP | 1 323 446 A2 | 7/2003 |
| JP | 2000-254226 | 9/2000 |
| JP | 2002-78798 | 3/2002 |
| JP | 2002-172165 | 6/2002 |
| JP | 2002-177395 | 6/2002 |
| WO | PCT/US99/17732 | 2/2000 |

* cited by examiner

*Primary Examiner*—Timothy L. Maust
(74) *Attorney, Agent, or Firm*—Arent Fox PLLC

(57) ABSTRACT

The drug solution container with a connector for communicating contains a drug solution container having at a tip end thereof an injection needle connecting part, and a hollow connector for communicating attached to a tip end of the drug solution container, and the connector for communicating contains a cylindrical guide part with a bottom capable of being slidably attached to an opening of a vial, and a hollow penetrating member provided at a center of the bottom of the guide part to penetrate the bottom. The penetrating member contains a penetrating needle at a tip end side with respect to the bottom, and a connecting part at a base end side with respect to the bottom, and the connecting part is connected to the injection needle connecting part through a fragile portion. According to the drug solution container with a connector for communicating, an operation for preparation of a drug solution can be easily carried out in a short period of time without causing injury of an operator or coring.

7 Claims, 18 Drawing Sheets

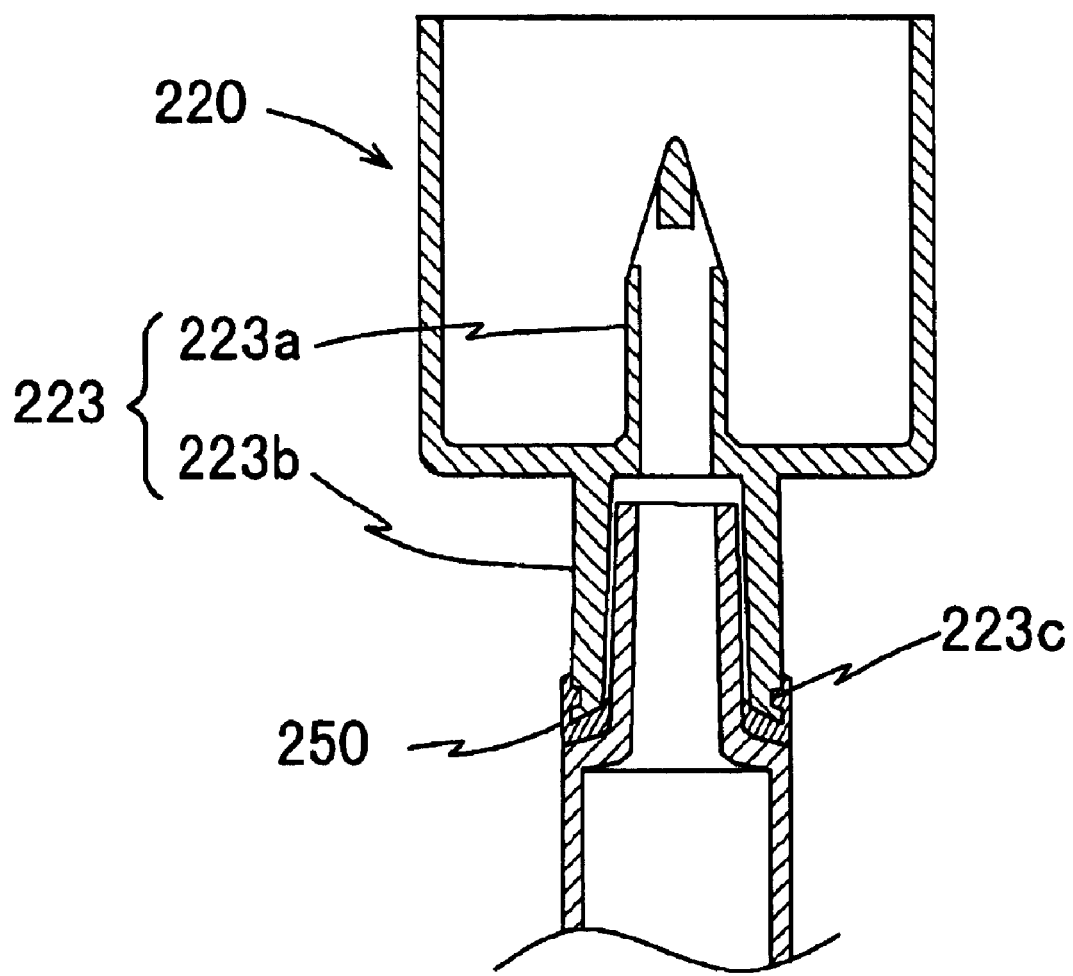

DRUG SOLUTION CONTAINER WITH A CONNECTOR FOR COMMUNICATING

BACKGROUND OF THE INVENTION

1. Field of the Invention

The present invention relates to a drug solution container with a connector for communicating that contains a drug solution having been charged therein. More particularly, it relates to a drug solution container with a connector for communicating that contains a drug solution having been charged therein, and that releasably has the connector for communicating, and the connector for communicating having a penetrating needle penetrating a sealing member at an opening part of a vial, and a vial guide.

2. Description of the Related Art

In general, a medical drug that is difficult to maintain stability in preparation and medical benefits in the form of a drug solution has been used in such a manner that the drug is stored by housing in a vial or the like in the form of a solid preparation, a powder preparation or a-freeze-dried preparation, and upon using the same, it is mixed with a resolvent using a syringe or the like to prepare a drug solution.

For example, in the case of a solid preparation housed in a vial, a resolvent housed in a vial or an ampoule is aspirated to a syringe (in alternative, a metallic injection needle for resolution is attached to a so-called prefilled syringe having a resolvent charged therein), and a metallic injection needle of the syringe is penetrated through a rubber plug of the vial. The resolvent is injected from the syringe to the vial to mix the resolvent with the solid preparation to prepare a drug solution, and after completing the operation for preparation of the drug solution, the drug solution is again aspirated to the syringe.

In the procedures using a syringe, however, since a metallic injection needle is necessarily used on preparation of a drug solution, there is such a possibility that an operator injured with the metallic injection needle, and in the case where the metallic injection needle is penetrated slantwise into a rubber plug of a vial, there is also such a possibility of coring of the rubber plug. Furthermore, it is more important that the operation is complicated to consume a prolonged period of time for the preparation.

In order to solve the problems, a technique shown in FIG. 18 has been proposed (see JP2002-78798A). In this invention, the interior of a main body of a container syringe 740, which also functions as a container, is sealed liquidtightly with two rubber stoppers of front-end 700 and back-end 710, and a drug solution is housed therein. At a front-end of a cartridge 750 of the syringe main body 740, a nozzle 761 of a nozzle head member 760 is provided, and an attachment part 771 of a penetrating needle member 770 is engaged in the nozzle 761.

It is said according to the invention that a liquid drug, such as a resolvent, can be easily and certainly injected from the container syringe to a vial having a powder preparation or the like housed therein, and there is no possibility that a drug solution containing scraps of a rubber plug is injected to a body of a patient.

However, because the penetrating member 770 and the injection needle connecting part 761 of the nozzle head member 760 are connected only by screwing in this invention, in the case where, for example, the cartridge 750 containing the drug solution 720 without using the front-end rubber stopper 700 is subjected to autoclaving, there is such a possibility that the drug solution housed therein is leaked from the connected part. In order to prevent the problem, the drug solution 720 housed in the cartridge 750 is sealed with the front-end rubber stopper 700, but it requires such a nozzle head member 760 that forms a drug solution path 762 on an outer wall of the front-end rubber stopper upon use, so as to complicate the production process. A rubber material as a raw material for the rubber stoppers 700 and 710 is expensive to raise the production cost. Furthermore, due to the absence of a vial guide, a tricky operation is required on penetration to a sealing member at an opening of a vial, and coring is liable to occur in the case where it is penetrated slantwise into a rubber plug. Moreover, there is such a possibility that a tip end 772 of the penetrating member 770 is contaminated by touch with fingers or the like.

BRIEF SUMMARY OF THE INVENTION

As a result of earnest investigations made by the inventors to solve the problems associated with the conventional techniques, the invention has been completed.

An object of the invention is to provide such a drug solution container with a connector for communicating that can be connected at the connector for communicating to a drug container liquidtightly and removably in an ordinary sterilizing process, that causes no injury of an operator and no coring, and that promotes an operation of preparing a drug solution in a short period of time.

The above-mentioned object and other objects of the present invention will be clarified further more in the following description, and these objects are attained by the present invention comprising the constitution mentioned below.

The invention relates to a drug solution container with a connector for communicating containing a drug solution container having at a tip end thereof an injection needle connecting part, and a hollow connector for communicating attached to a tip end of the drug solution container; the connector for communicating containing a cylindrical guide part with a bottom capable of being slidably attached to an opening of a vial, and a hollow penetrating member provided at a center of the bottom of the guide part to penetrate the bottom; the penetrating member containing a penetrating needle at a tip end side with respect to the bottom, and a connecting part at a base end side with respect to the bottom; and the connecting part being connected to the injection needle connecting part.

The connecting part of the penetrating member may be fitted on an outside of the injection needle connecting part, and the connecting part of the penetrating member may be adhered to the injection needle connecting part easily removably through a fragile portion.

The connector for communicating may be easily removed from the drug solution container by rotating the connector for communicating relative to the drug solution container to remove the fragile portion.

The connecting part of the penetrating member may be connected by screwing to the injection needle connecting part.

A remaining part may be consecutively provided through a breaking part on the connecting part of the penetrating member at a base end side with respect to a screw forming part, the remaining part may be engaged with the injection needle connecting part, and the breaking part may be broken upon releasing the screwing of the connecting part of the penetrating member and the injection needle connecting part.

The connecting part of the penetrating member may be connected by engaging to the injecting needle connecting part.

A remaining part may be consecutively provided through a breaking part on a base part of the connecting part of the penetrating member, the remaining part may be engaged with the injection needle connecting part to connect the connecting part of the penetrating member to the injection needle connecting part, and the breaking part may be broken upon separating the connecting part of the penetrating member and the injection needle connecting part.

A seal material may intervene between an inside of the connecting part of the penetrating member and a tip end of the injection needle connecting part.

The drug solution container may comprise a barrel with an open base end having an injection needle connecting part at a tip end thereof, and a gasket inserted from the open base end of the barrel liquidtightly and slidably into the barrel.

BRIEF DESCRIPTION OF THE DRAWINGS

FIG. 3 is a partial vertical cross sectional view showing another embodiment of the invention.

DETAILED DESCRIPTION OF THE INVENTION

Figure 1:
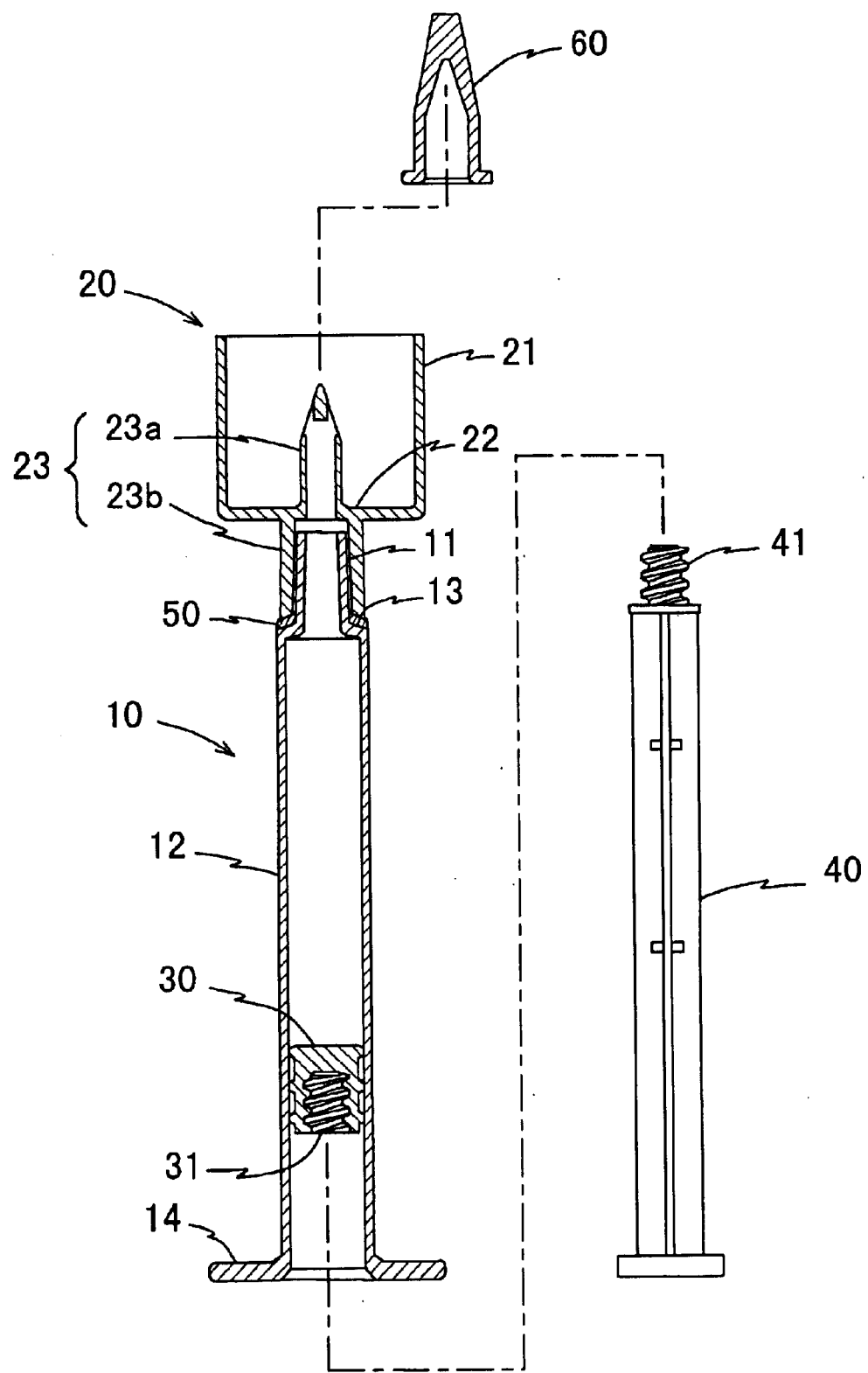
FIG. 1 is a vertical cross sectional view showing an embodiment of the invention.

Embodiments of the invention are schematically described, and FIG. 1 is a vertical cross sectional view showing an embodiment of the invention, in which a fragile portion is formed with a mixture of materials forming a drug solution container and a connecting part of a penetrating member.

Figure 2:
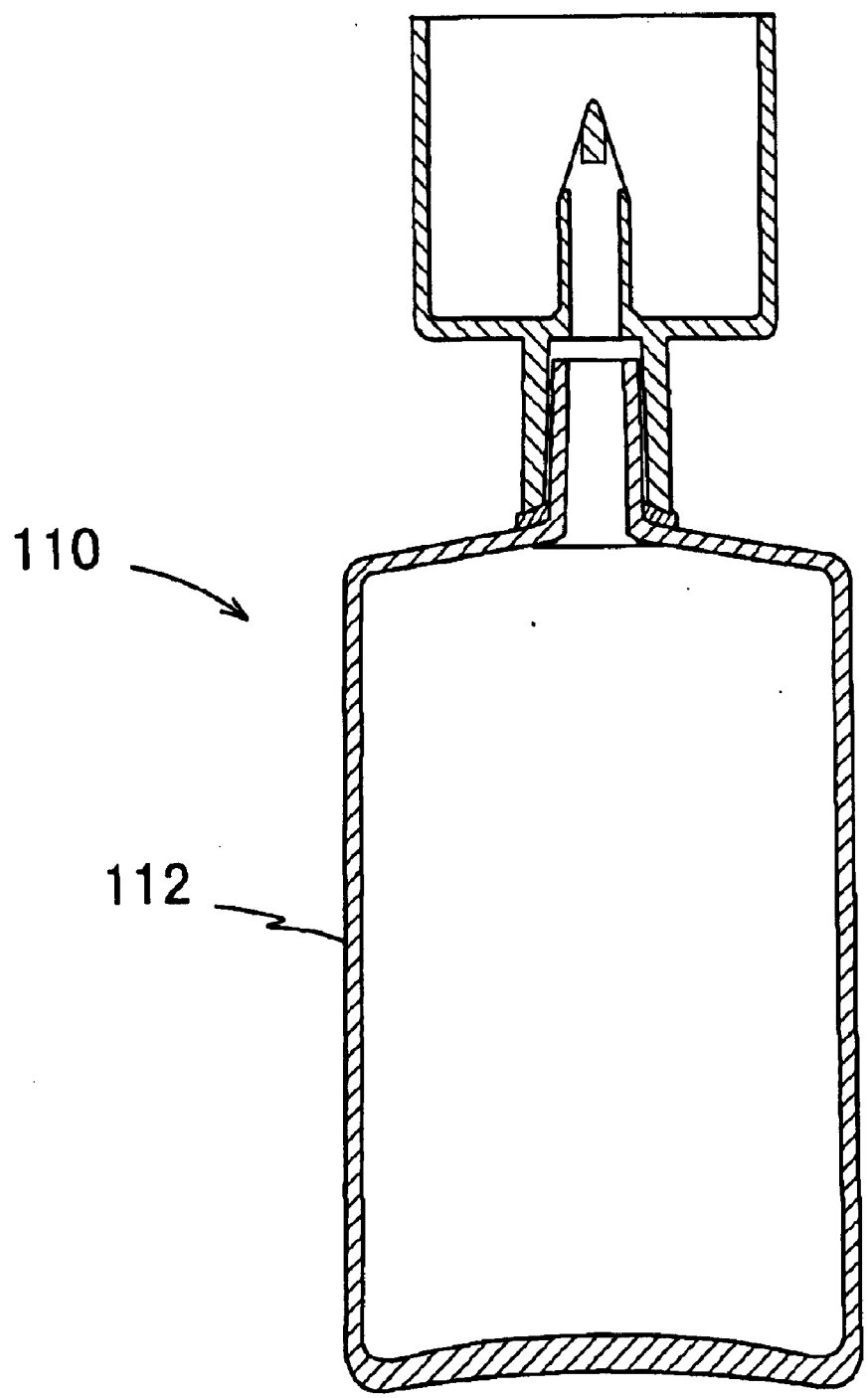
FIG. 2 is a vertical cross sectional view showing another, embodiment of the invention.

FIG. 2 is a vertical cross sectional view showing another embodiment of the invention, in which a fragile portion is formed with a mixture of materials forming a drug solution container and a connecting part of a penetrating member, and a bottle is employed as the drug solution container.

FIG. 3 is a partial vertical cross sectional view showing still another embodiment of the invention, in which a fragile portion is formed with a mixture of materials forming a drug solution container and a connecting part of a penetrating member, and a part engaging with the fragile portion is provided on the connecting part.

Figure 4A:
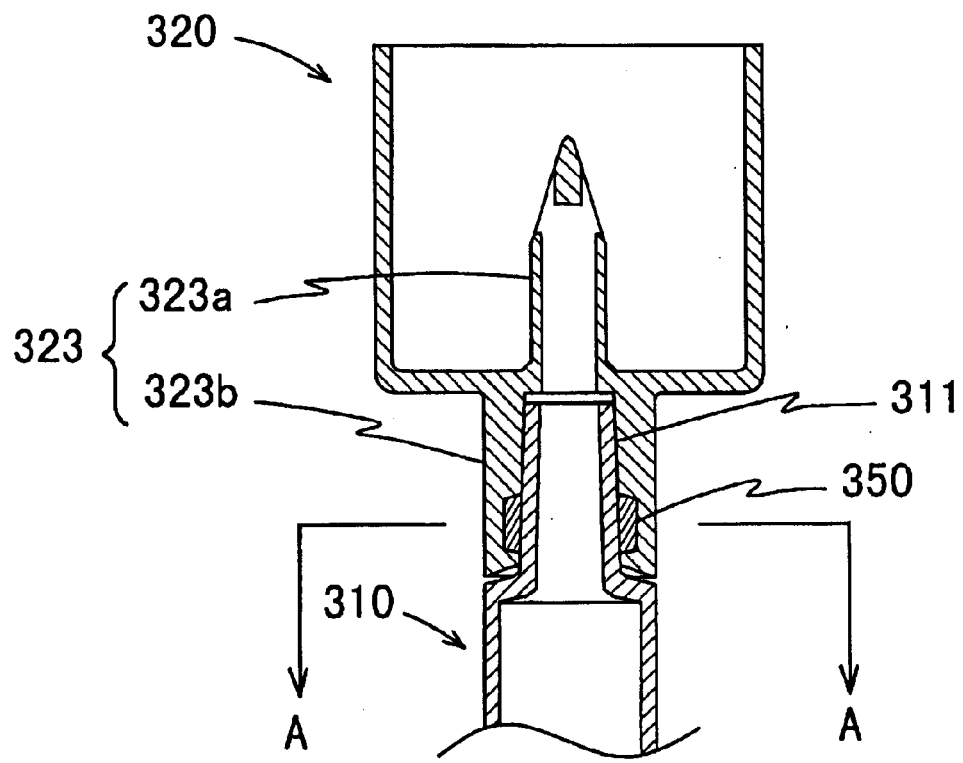
FIG. 4 shows another embodiment of the invention, (a) of FIG. 4 is a partial vertical cross sectional view, and (b) of FIG. 4 is a cross sectional view on line A—A.
Figure 4B:
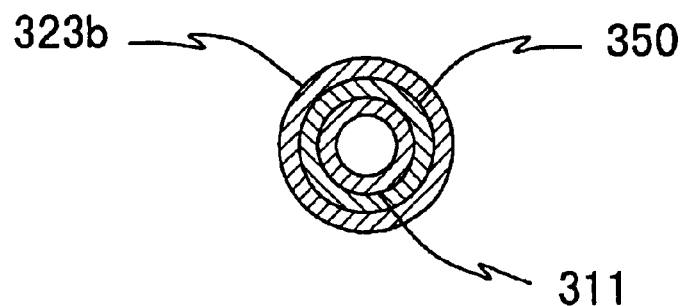

FIG. 4 is a diagram showing a further embodiment of the invention. A fragile portion formed with at least one material selected from a thermoplastic elastomer, a silicone elastomer and butyl rubber is provided on an inside of a connecting part of a penetrating member. (a) of FIG. 4 is a partial vertical cross sectional view, and (b) of FIG. 4 is a cross sectional view on line A—A.

FIG. 5 is a partial vertical cross sectional view showing a still further embodiment of the invention, in which a connector for communicating is entirely formed with at least one material selected from a thermoplastic elastomer, a silicone elastomer and butyl rubber, and an anchor is vertically provided from a backside of a bottom of a guide part. (a) of FIG. 5 is a partial vertical cross sectional view, and (b) of FIG. 5 is a cross sectional view on line B—B.

Figure 6A:
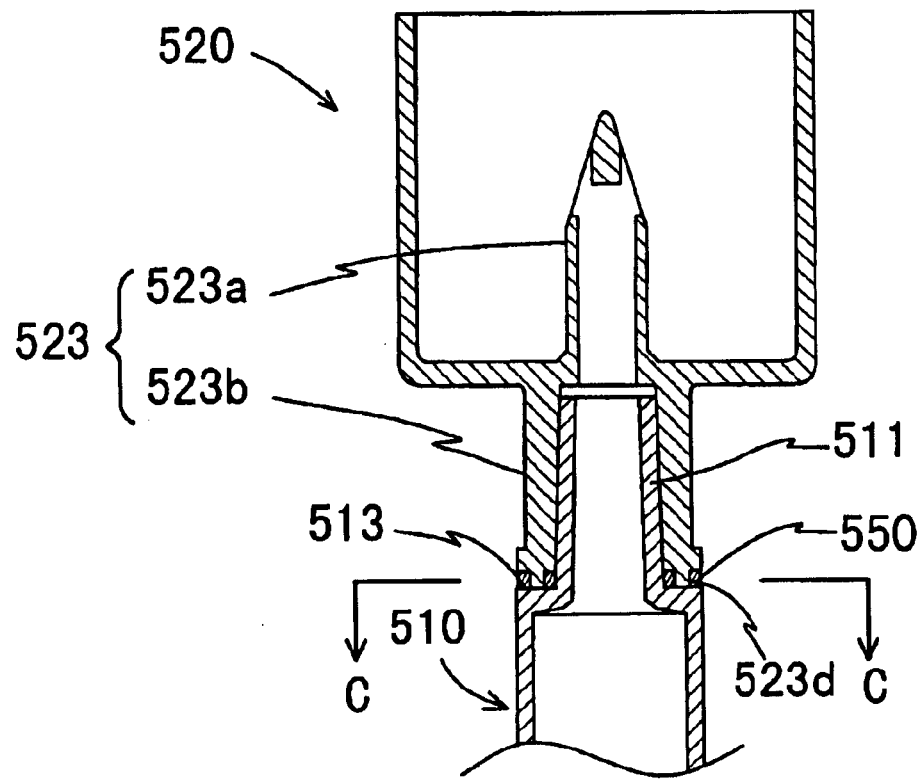
FIG. 6 shows another embodiment of the invention, (a) of FIG. 6 is a partial vertical cross sectional view, and (b) of FIG. 6 is a cross sectional view on line C—C.
Figure 6B:
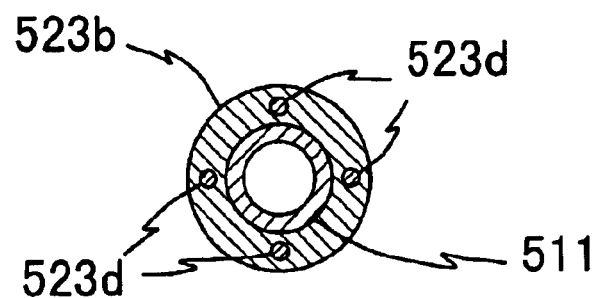

FIG. 6 a partial vertical cross sectional view-showing a still further embodiment of the invention, in which a fragile portion having a square ring shape formed with at least one material selected from a thermoplastic elastomer, a silicone elastomer and butyl rubber is provided on a base end of a connector for communicating. (a) of FIG. 6 is a partial vertical cross sectional view, and (b) of FIG. 6 is a cross sectional view on line C—C.

Figure 7:
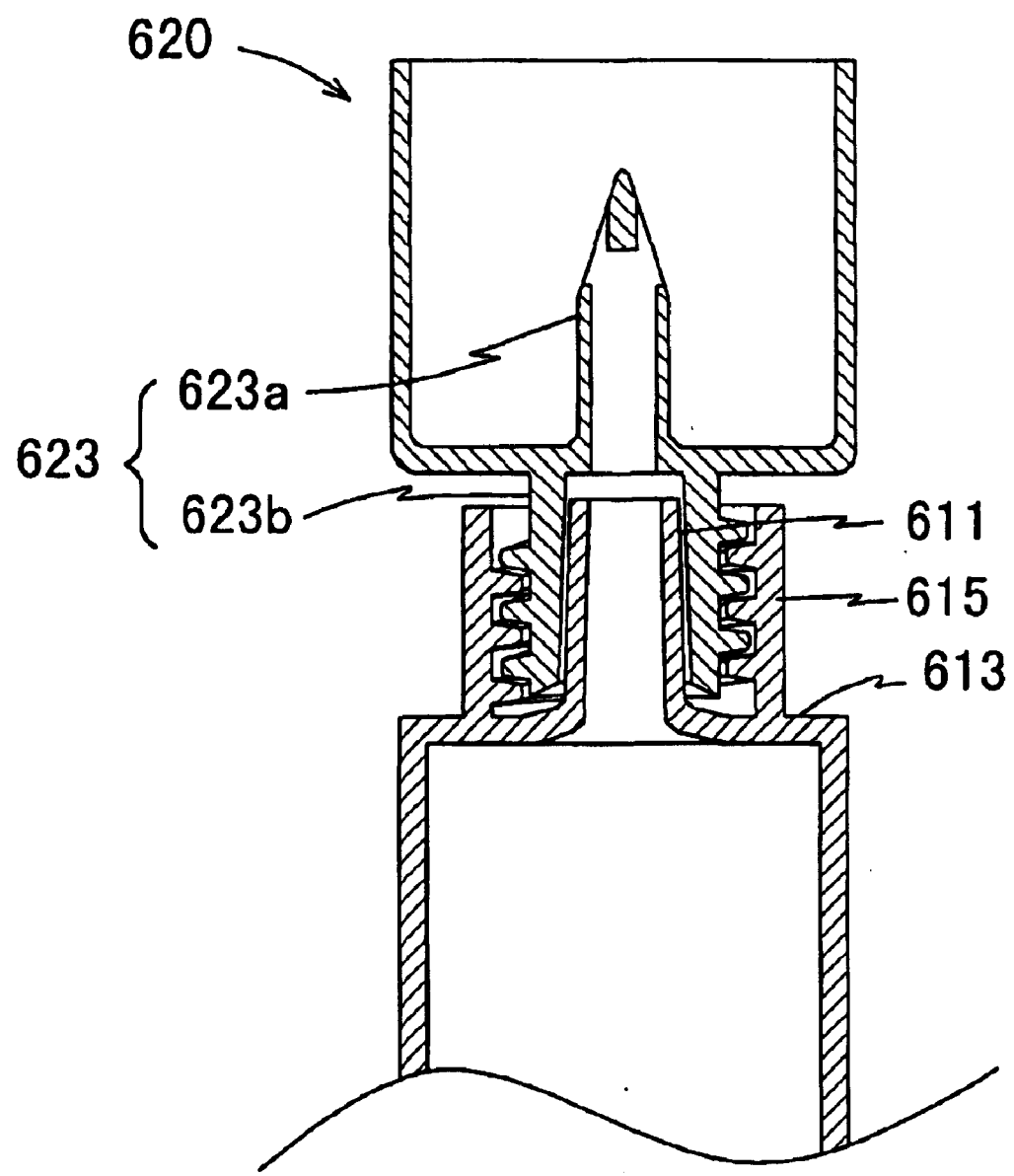
FIG. 7 is a partial vertical cross sectional view showing another embodiment of the invention.

FIG. 7 is a partial vertical cross sectional view showing a still further embodiment of the invention, in which a connector for communicating and a drug solution container are connected by screwing.

Figure 8:
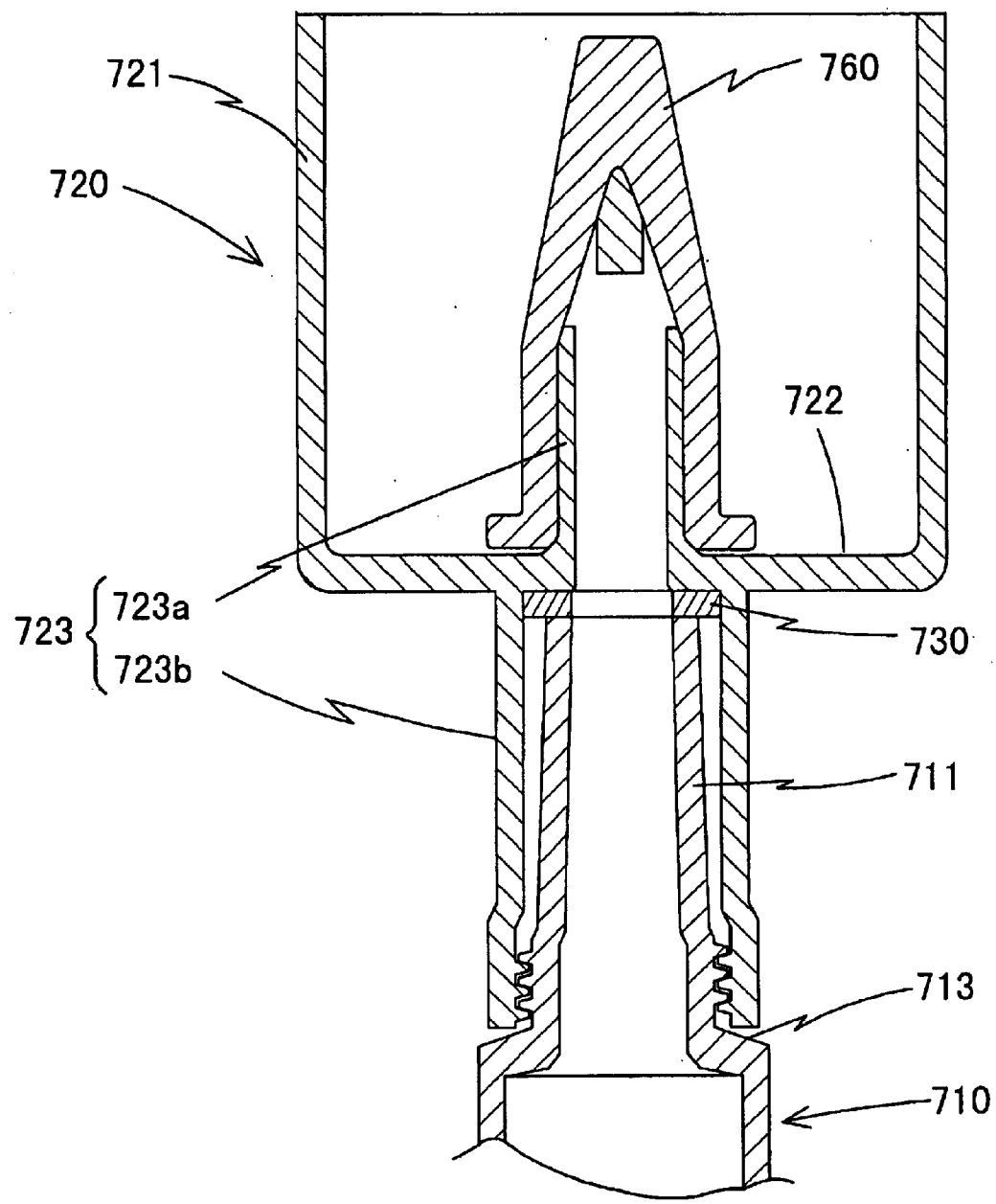
FIG. 8 is a partial vertical cross sectional view showing another embodiment of the invention.

FIG. 8 is a partial vertical cross sectional view showing a still further embodiment of the invention, in which a connector for communicating and a drug solution container are connected by screwing.

Figure 9:
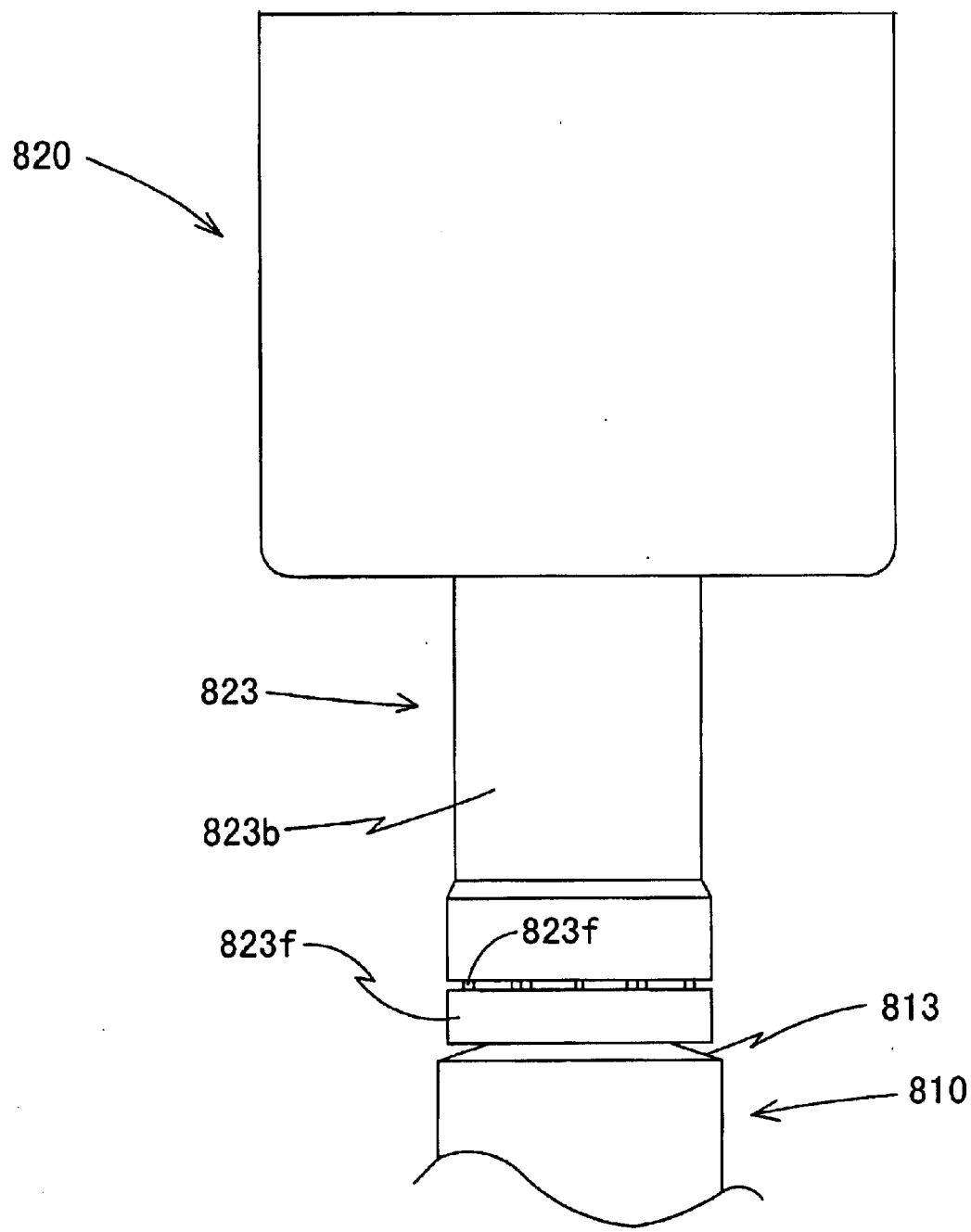
FIG. 9 is a partial front view showing another embodiment of the invention.
Figure 10:
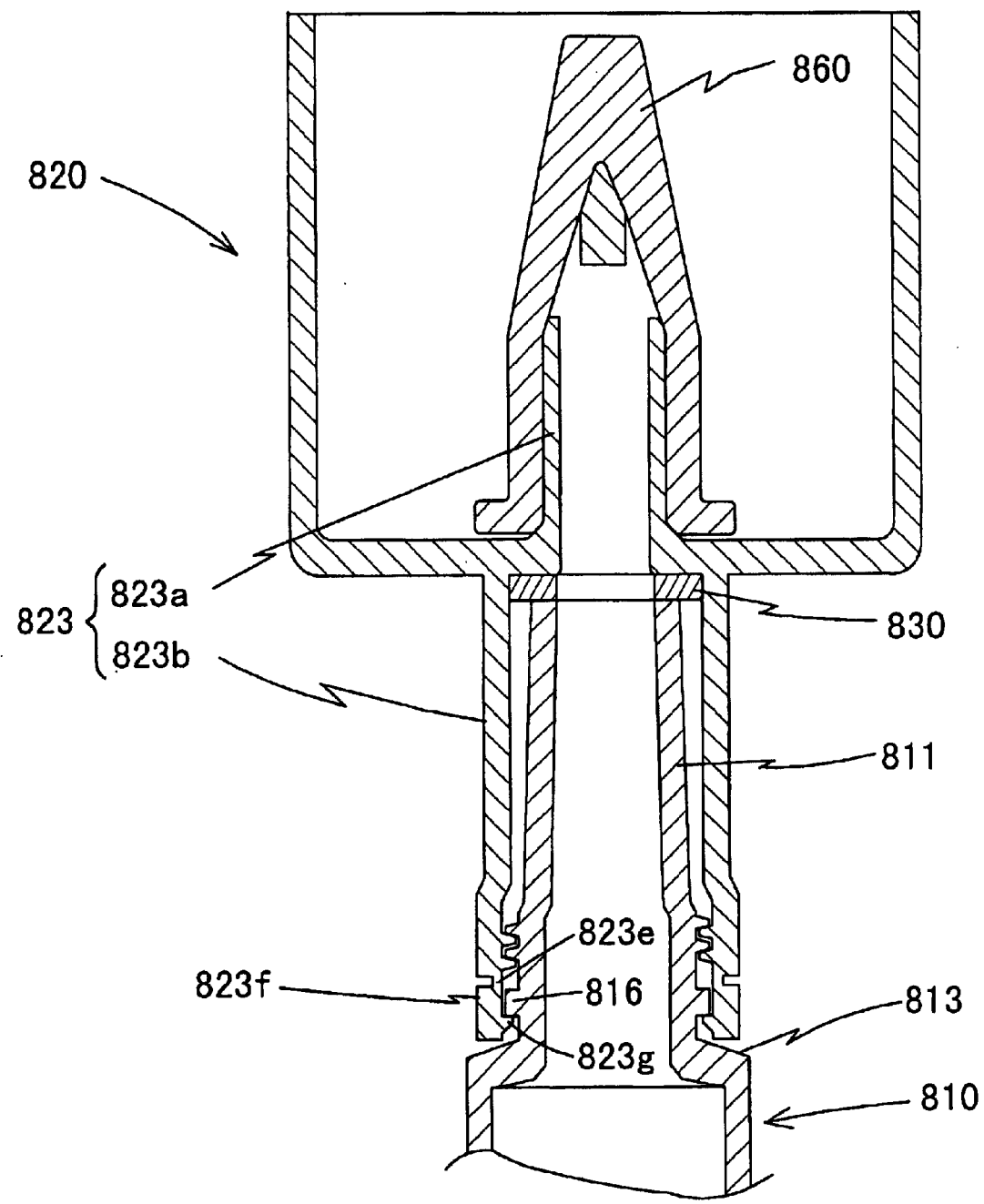
FIG. 10 is a vertical cross sectional view of FIG. 9.

FIG. 9 is a partial front view showing a still further embodiment of the invention, and FIG. 10 is a vertical cross sectional view of FIG. 9, in which a connector for communicating and a drug solution container are connected by screwing.

Figure 11:
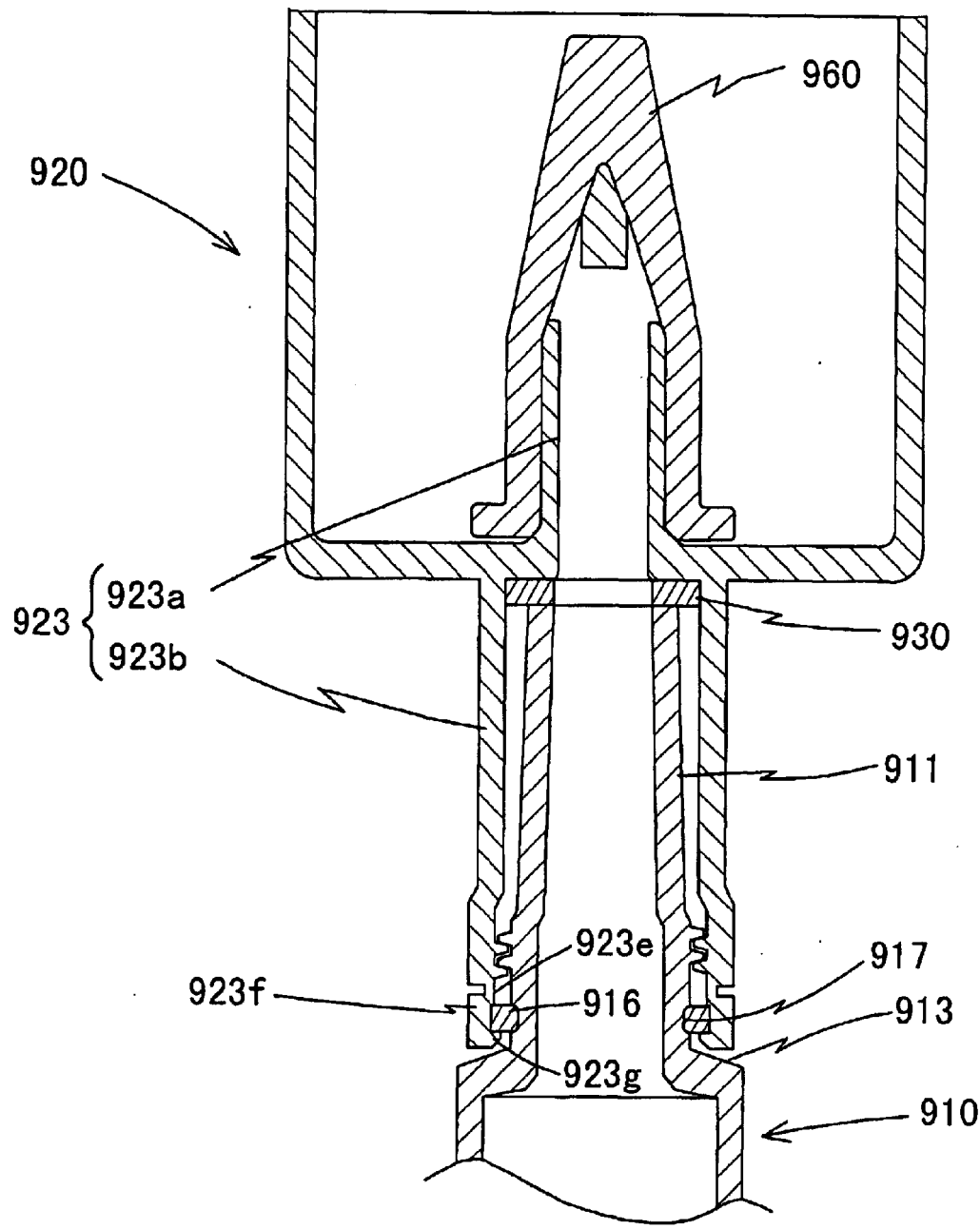
FIG. 11 is a partial vertical cross sectional view showing another embodiment of the invention.

FIG. 11 is a partial vertical cross sectional view showing a still further embodiment of the invention, in which a connector for communicating and a drug solution container are connected by screwing.

Figure 12:
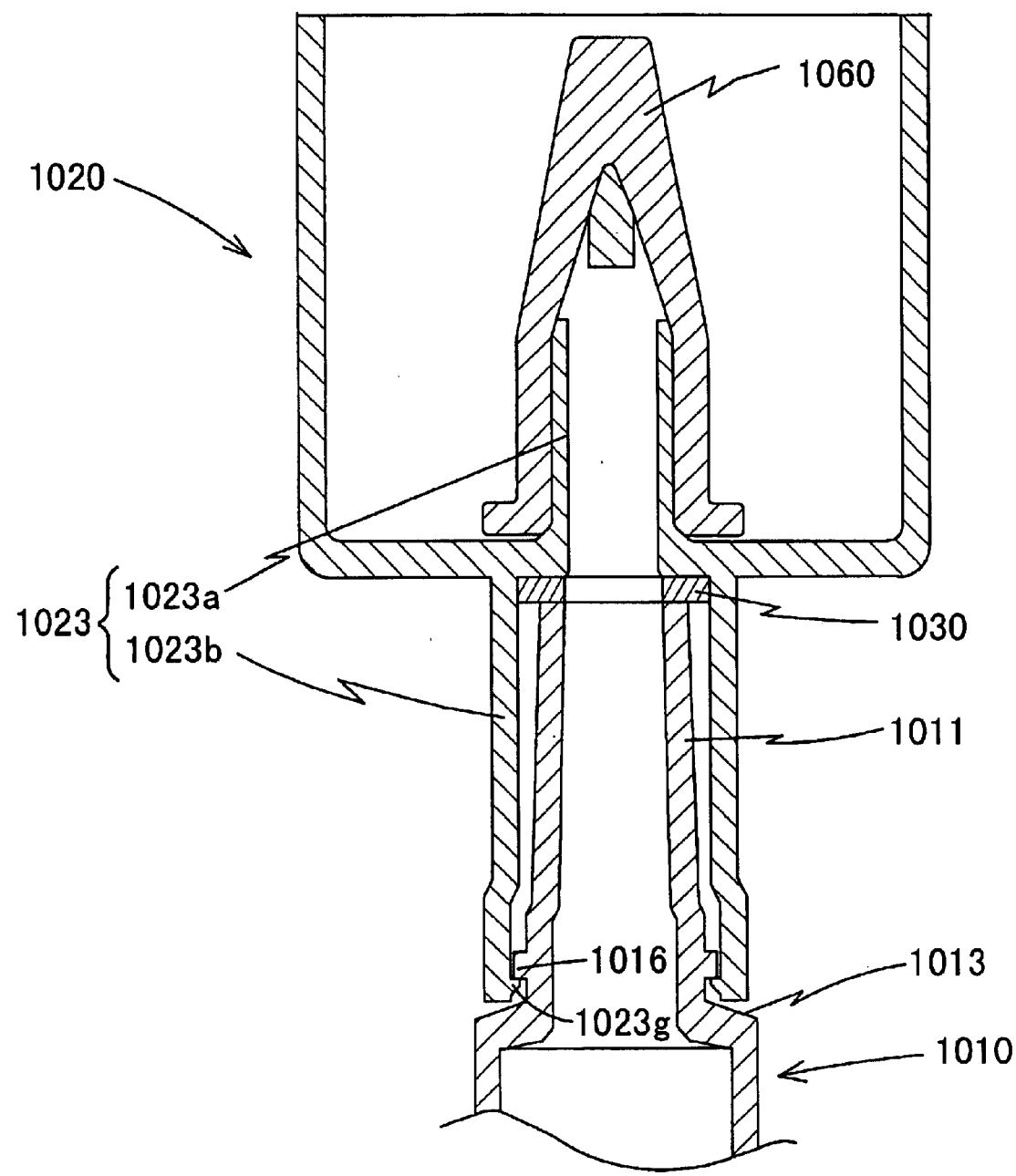
FIG. 12 is a partial vertical cross sectional view showing another embodiment of the invention.

FIG. 12 is a partial vertical cross sectional view showing a still further embodiment of the invention, in which a connector for communicating and a drug solution container are connected by engaging.

Figure 13:
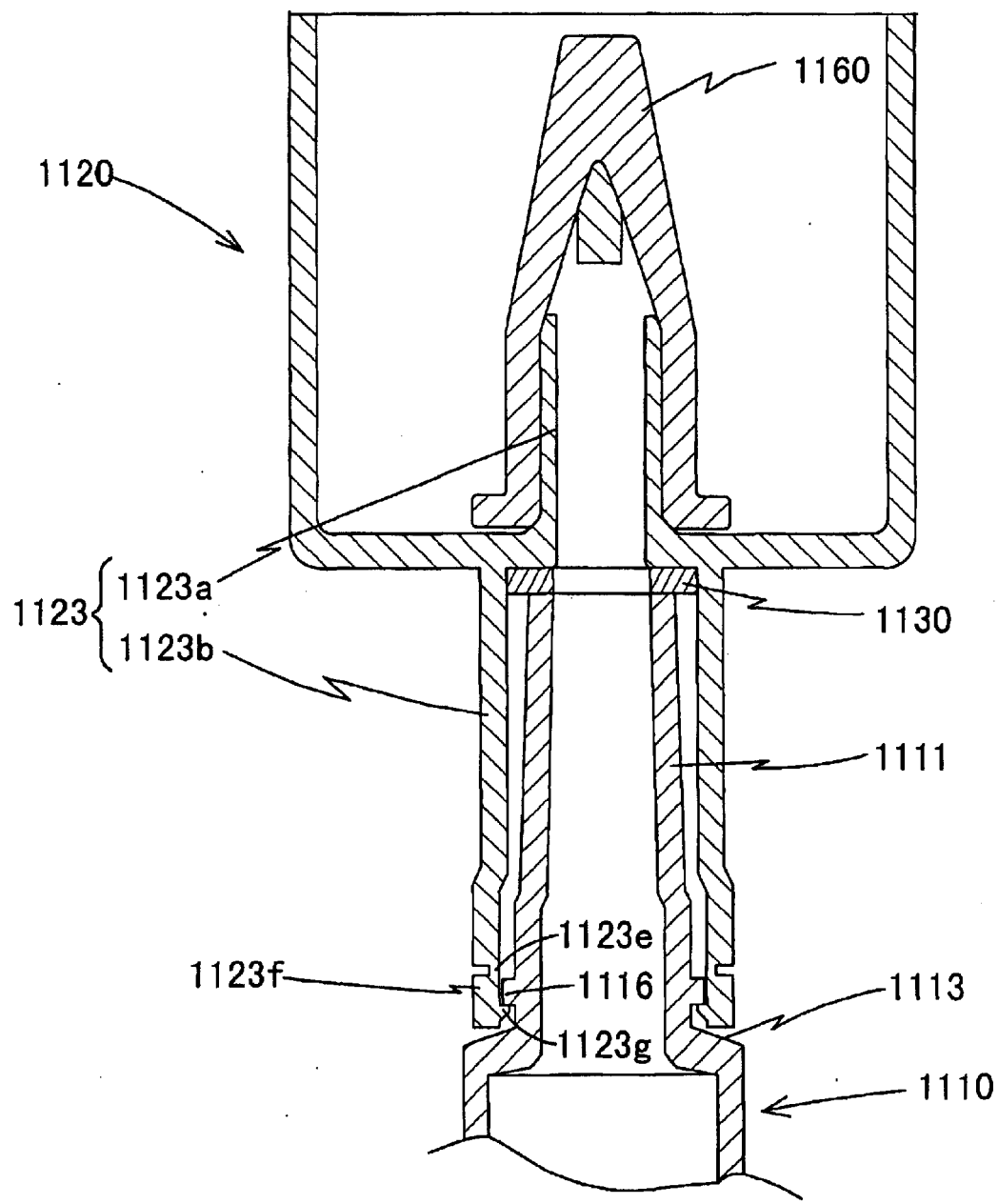
FIG. 13 is a partial vertical cross sectional view showing another embodiment of the invention.

FIG. 13 is a partial vertical cross sectional view showing a still further embodiment of the invention, in which a connector for communicating and a drug solution container are connected by engaging.

Figure 14:
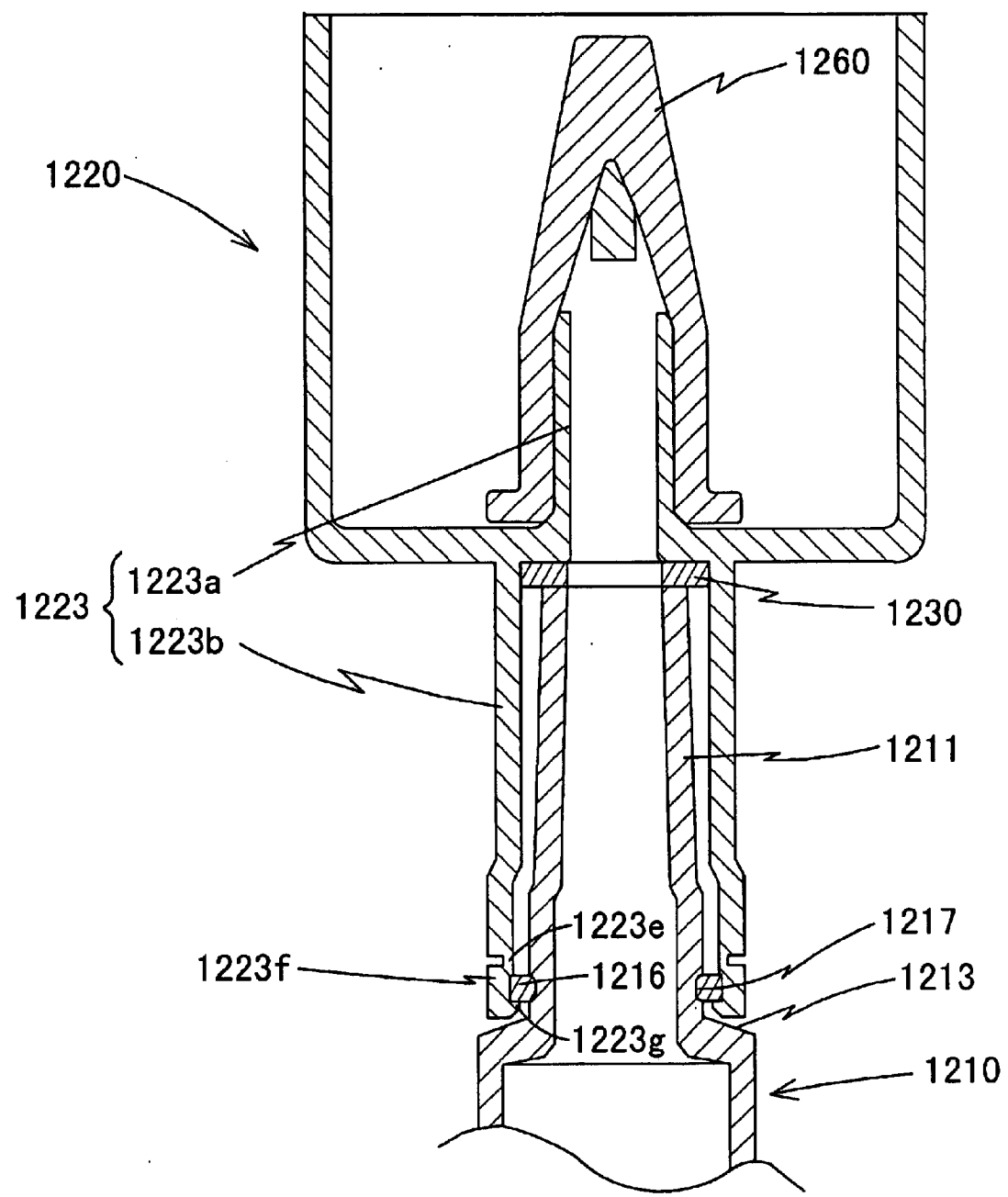
FIG. 14 is a partial vertical cross sectional view showing another embodiment of the invention.

FIG. 14 is a partial vertical cross sectional view showing a still further embodiment of the invention, in which a connector for communicating and a drug solution container are connected by engaging.

Figure 15:
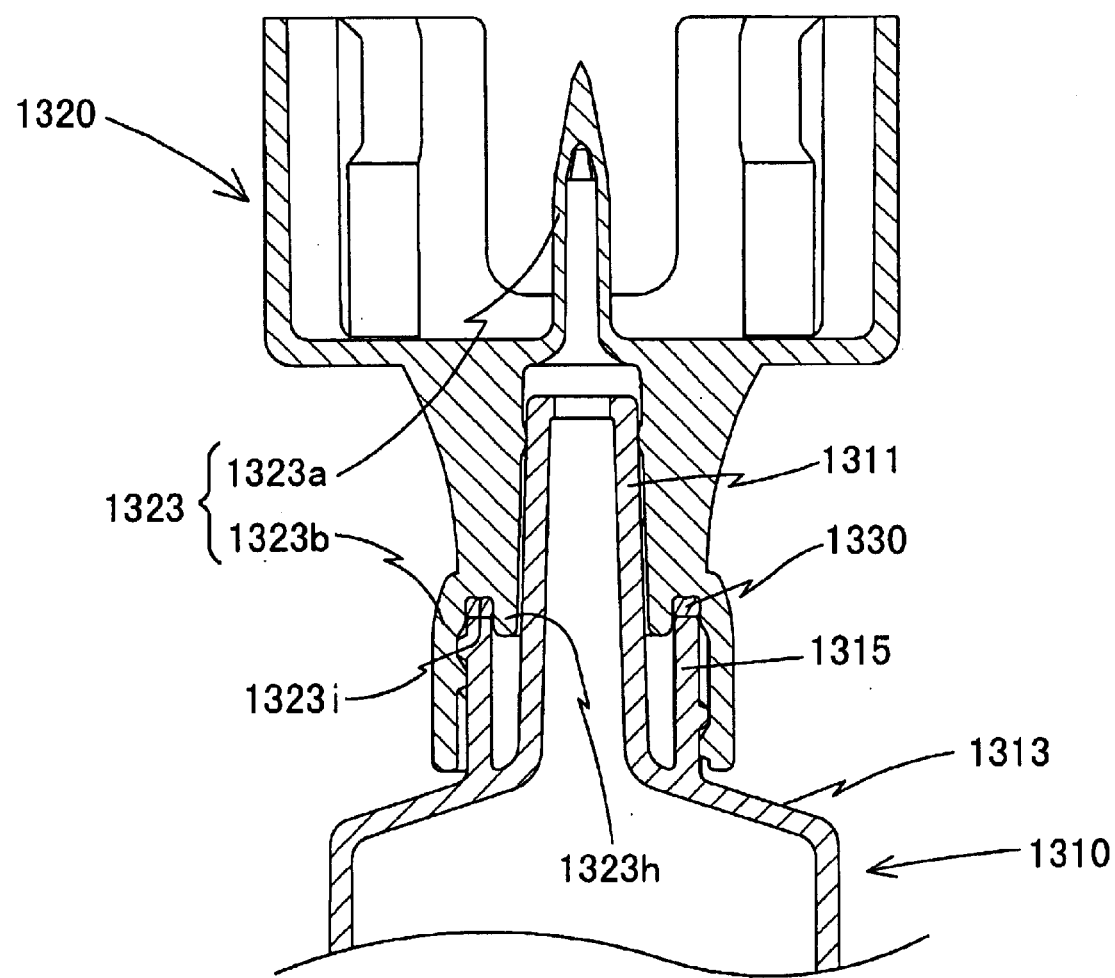
FIG. 15 is a partial vertical cross sectional view showing another embodiment of the invention.

FIG. 15 is a partial vertical cross sectional view showing a still further embodiment of the invention, in which a connector for communicating and a drug solution container are connected by screwing.

Figure 16:
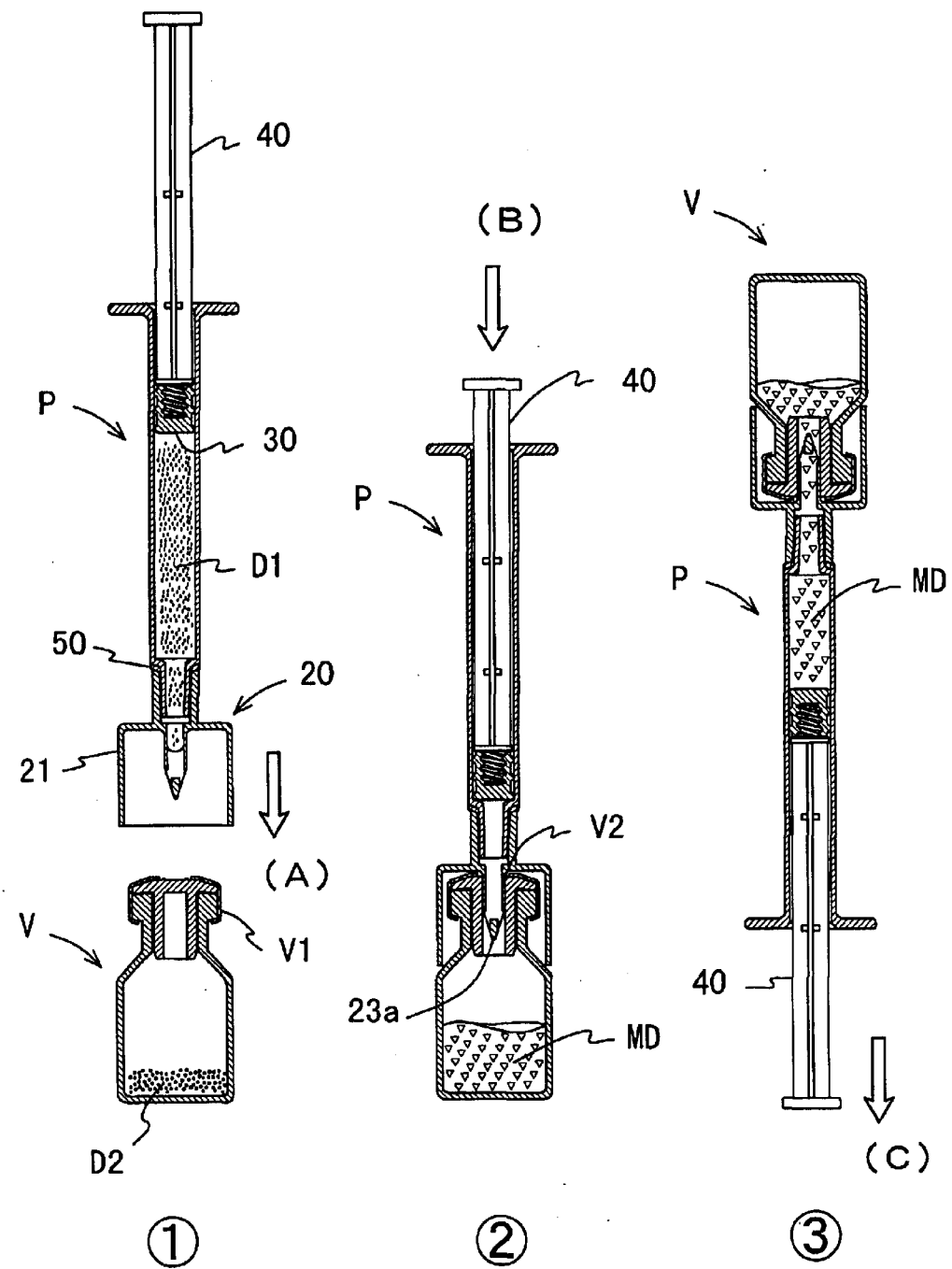
FIG. 16 is a cross sectional view showing the use of the drug solution container with a connector for communicating according to the invention.
Figure 17:
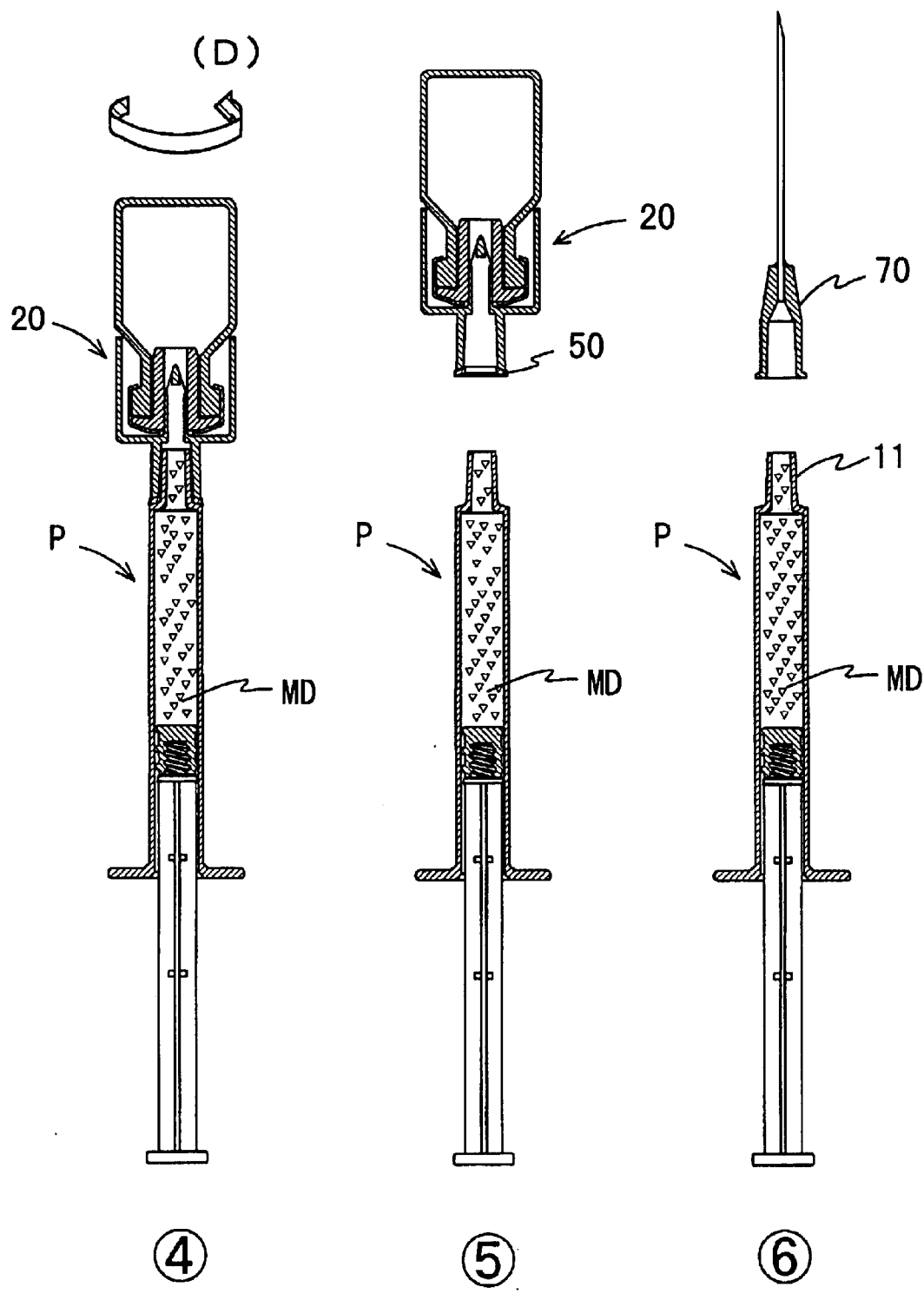
FIG. 17 is a cross sectional view showing the use of the drug solution container with a connector for communicating according to the invention.
Figure 18:
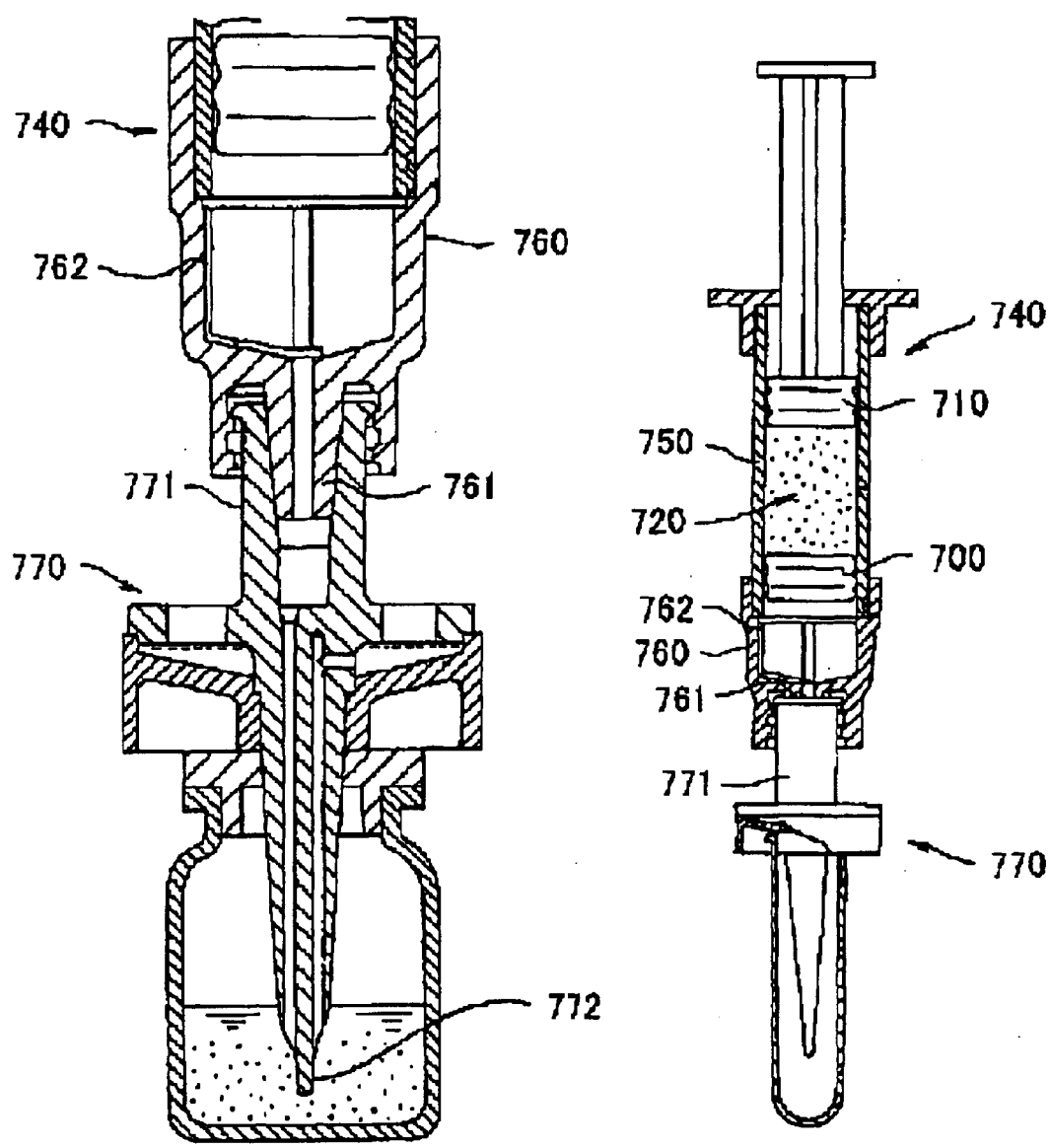
FIG. 18 is a cross sectional view showing a prior art.

FIGS. 16 and 17 are cross sectional views showing the use of the drug solution container with a connector for communicating according to the invention.

The term "blocking" used in this specification means such a phenomenon that a thermoplastic elastomer, a silicone elastomer and butyl rubber and a polyolefin are adhered to each other, and they are difficult to be released.

As the invention is described in detail with reference to embodiments, in an embodiment shown in FIG. 1, a drug solution container with a connector for communicating according to the invention has a drug solution container 10 having an injection needle connecting part 11 at a tip end thereof, and a hollow connector for communicating 20 provided at the tip end of the drug solution container 10. The connector for communicating 20 has a cylindrical guide part with a bottom 22 capable of being slidably attached to an opening of a vial, and a hollow penetrating member 23 provided at a center of the bottom 22 of the guide part 21 to penetrate the bottom 22. The penetrating member 23 has a penetrating needle 23a at a tip end side with respect to the bottom 22, and a connecting part 23b at a base end side with respect to the bottom 22, and the connecting part 23b is connected liquidtightly to the injection needle connecting part 11.

As the drug solution container 10, such a syringe type drug solution container is preferably employed that contains a barrel 12 with an open base end having an injection needle connecting part 11 at a tip end thereof, and a gasket 30 inserted from the open base end of the barrel 12 liquidtightly and slidably into the barrel 12. The barrel 12 is generally a cylindrical member formed with a polyolefin resin, such as polypropylene and polyethylene, and a shoulder part 13 is formed from a base end of the injection needle connecting part 11 over an outer circumference of a tip end face of the barrel. A fingerhold flange 14 is provided at the base end of the barrel 12. The gasket 30 is formed with butyl rubber, a thermoplastic elastomer or the like, and inserted from a base end of the barrel 12 liquidtightly and slidably into the barrel 12. An engaging means, such as a female screw 31, is provided at a base end of the gasket 30, and can be screwed with a male screw 41 provided at a tip end of a plunger 40.

The drug solution container 110 may be a bottle 112 that is formed with a flexible material, such as polyethylene and polypropylene, and can be easily deformed by pressing, as shown in FIG. 2.

As the connector for communicating 20 shown in FIG. 1 is described in detail, the connector for communicating 20 is generally formed with polypropylene, an ABS resin, polyethylene, a mixture of polypropylene and polyethylene, or the like, and, as described above, contains the cylindrical guide part 21 with the bottom 22 capable of being slidably attached to the opening of the vial, and the hollow penetrating member 23 provided at the center of the bottom 22 of the guide part 21 to penetrate the bottom 22, and the penetrating member 23 contains the penetrating needle 23a at the tip end side with respect to the bottom 22, and the connecting part 23b at the base end side with respect to the bottom 22. An interior of the connecting part 23b has luer taper and is fitted on an outside of the injection needle connecting part 11 of the drug solution container 10, and a tip end of the connecting part 23b is adhered easily removably to the shoulder part 13 of the drug solution container 10 through a fragile portion 50. According to the configuration, upon autoclaving the drug solution container with a connector for communicating according to the invention, invasion of water from the fitting part of the injection needle connecting part 11 and the connecting part 23b can be prevented. It is preferred that the fragile portion 50 is easily removed by applying rotation to the connector for communicating 20 relative to the drug solution container 10.

The fragile portion 50 is formed generally, for example, with a mixed material of such a material that is poor compatibility with a material for forming the drug solution container 10 but is good compatibility with a material for forming the penetrating member 23, such as a mixed material of a material forming the drug solution container 10 and a material forming the penetrating member 23. More specifically, for example, in the case where the drug solution container 10 is formed with polypropylene as a major component, and the penetrating member 23 is formed with polyethylene as a major component, the fragile portion 50 is formed with a material containing a mixture of polypropylene and polyethylene as a major component, whereby the drug solution container 10 and the penetrating member 23 are weakly welded together removably through the fragile portion 50. The fragile portion 50 thus formed is removed accompanied with the connector for communicating 20 from the drug solution container 10 upon rotating the connector for communicating 20 with respect to the drug solution container 10. In the case where the fragile portion 50 is formed with a material that is poor compatibility with a material for forming the penetrating member 23 to provide a weak adhesion force therebetween, such a structure shown in FIG. 3 may be employed in that an engaging part 223c is provided at a connecting part 223b of a penetrating member 223, whereby separation of a fragile portion 250 and a connector for communicating 220 is physically suppressed.

The fragile portions 50 and 250 may be formed by insert molding or by two-color molding.

In another embodiment of the invention shown in FIG. 4, a fragile portion 350 formed with at least one material selected from a thermoplastic elastomer, a silicone elastomer and butyl rubber is provided on an inside of a connecting part 323b of a penetrating member 323 of a connector for communicating 320, and a drug solution container 310 and the connector for communicating 320 are connected liquidtightly and removably by blocking of an injection needle connecting part 311 and a fragile portion 350. The fragile portion 350 may be formed by insert molding or by two-color molding, or in alternative, it may be separately molded and then fit inside the connecting part 323b.

A method of connecting the fragile portion 350 to the injection needle connecting part 311 by blocking in the embodiment shown in FIG. 4 will be described. A connecting part 323b of a penetrating member 323 having provided with the fragile portion 350 formed with a thermoplastic elastomer, a silicone elastomer or butyl rubber is attached by insertion to an injection needle connecting part 311 of a drug solution container 310, so as to contact the fragile portion 350 closely to the injection needle connecting part 311, and then the whole assembly is subjected to autoclaving, for example, at 115° C. for 30 minutes or at 121° C. for 20 minutes, which are generally employed conditions upon production of drugs, whereby a thermoplastic elastomer, a silicone elastomer or butyl rubber forming the fragile portion 350 causes blocking with the injection needle connecting part 311 which is formed with a polyolefin resin to connect the connector for communicating 320 and the drug solution container 310 liquidtightly. Upon rotating the connector for communicating 320 relative to the drug solution container 310, the fragile portion 350 is removed from the injection needle connecting part 311, and as a result, the connector for communicating 320 and the drug solution container 310 can be separated from each other.

Figure 5A:
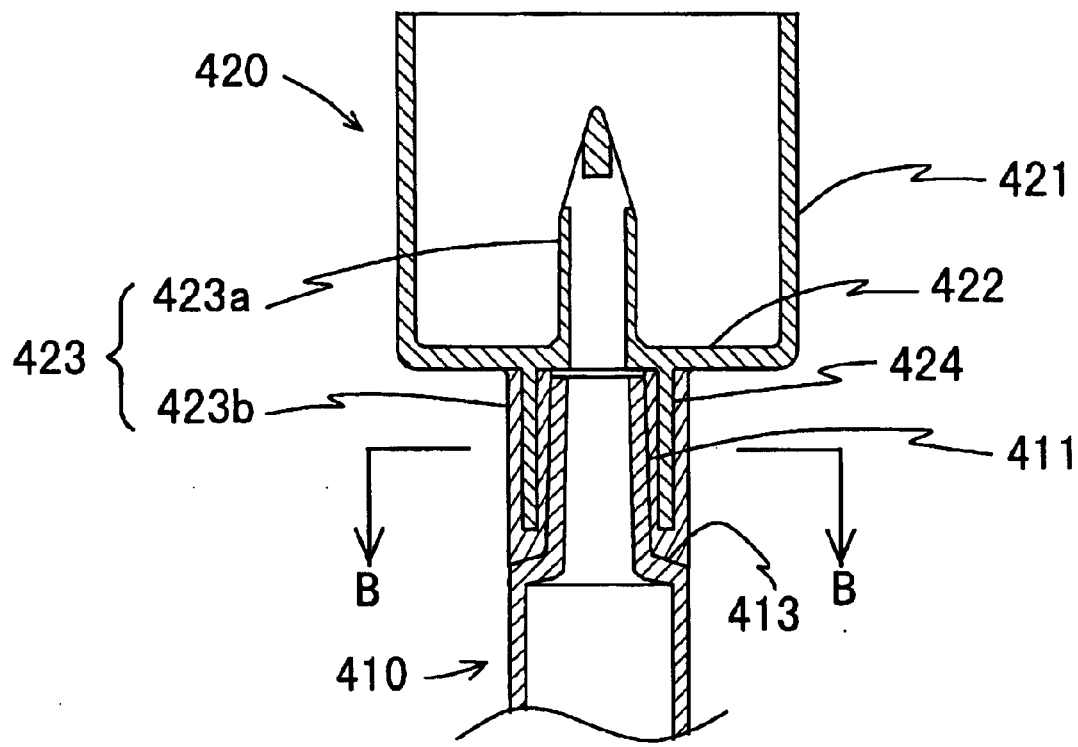
FIG. 5 shows another embodiment of the invention, (a) of FIG. 5 is a partial vertical cross sectional view, and (b) of FIG. 5 is a cross sectional view on line B—B.
Figure 5B:
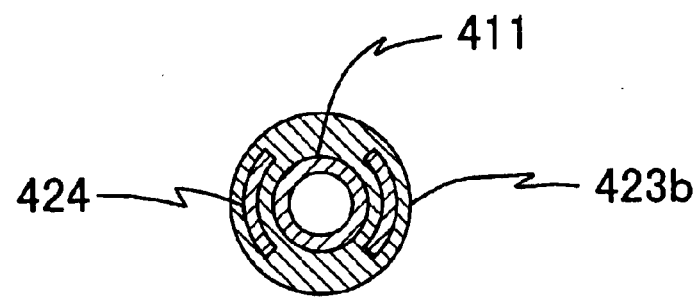

In another embodiment of the invention shown in FIG. 5, a connecting part 423b of a penetrating member 423 of a connector for communicating 420 is entirely formed with a thermoplastic elastomer, a silicone elastomer, butyl rubber or the like, and blocking is caused at an inside of the connecting part 423b and an outside and a shoulder part 413 of an injection needle connecting part 411, so as to connect the connecting part 423b, the injection needle connecting part 411 and the shoulder part 413 liquidtightly and removably. An anchor 424 is vertically provided from a backside of a bottom 422 of a guide part 421 into an interior of the connecting part 423b. The provision of the anchor 424 prevents, upon rotating the connector for communicating 420 relative to the drug solution container 410, the connector for communicating 420 from being removed by leaving only the connecting part 423b blocked with the injection needle connecting part 411 on the drug solution container 410. While the anchor 424 shown in FIGS. 5A and 5B is constituted with two members each having a partially cylindrical shape with an arc part, an anchor having an arbitrary shape may be employed as long as it locks the backside of the bottom of the guide part with the connecting part to prevent other parts of the connector for communicating than the connecting part from being removed from the drug solution container upon rotating the connector for communicating relative to the drug solution container.

In another embodiment of the invention shown in FIG. 6, a fragile portion 550 having a square ring shape formed with at least one material selected from a thermoplastic elastomer, a silicone elastomer and butyl rubber is provided between an end tip of a connecting part 523b of a connector for communicating 520 and a shoulder part 513 of a drug solution container 510, and the connector for communicating 520 and the drug solution container 510 are connected liquidtightly and removably by blocking of the fragile portion 550 and the shoulder part 513. Furthermore, it is preferred to provide a protrusion 523d at a base end of the connecting part 523b, whereby upon rotating the connector for communicating 520 relative to the drug solution container 510 upon use, the fragile portion 550 is prevented from being removed from the connector for communicating 520 by a rotation force, so that the fragile portion 550 is rotated accompanied with the connector for communicating 520. While a square ring is employed as a fragile portion in this embodiment, such other rings may also be employed that can connect the connector for communicating and the syringe liquidtightly and removably by blocking. The protrusion may also be provided on the side of the shoulder part.

While the material of the fragile portion 350 in FIG. 4, the connecting part 423b of the penetrating member 423 in FIG. 5, and the fragile portion 550 in a square ring shape in FIG. 6 are preferably a thermoplastic elastomer, a silicone elastomer or butyl rubber, as described in the foregoing, the material is not particularly limited as long as it can seal each of the injection needle connecting parts 311, 411 and 511 liquidtightly and removably by blocking.

As shown in FIG. 7, instead of provision of a fragile portion, a connecting part 623b of a penetrating member 623 may be connected to an injection needle connecting part 611 by screwing liquidtightly and releasably. In FIG. 7, the connecting part 623b of the penetrating member 623 is not directly screwed in the injection needle connecting part 611, but they are screwed each other in the following manner. That is, a cylindrical wall 611 concentrically surrounding the injection needle connecting part 611 is provided at a shoulder part 613, and a male screw on an outside of the connecting part 623b is screwed in a female screw on an inside of the cylindrical wall 615. The inside of the connecting part 623b and the outside of the injection needle connecting part 611 are closely in contact with each other liquidtightly.

In another embodiment shown in FIG. 8, a male screw on an outside of a base part of an injection needle connecting part 711 of a drug solution container 710 is screwed in a female screw on an inside of a base part of a connecting part 723b of a penetrating member 723. A seal material 730, examples of which include an O-ring and a packing, intervenes between a bottom 722 of a guide part 721 inner than the connecting part 723b and a tip end of the injection needle connecting part 711, whereby a connector for communicating 720 is connected to the injection needle connecting part 711 liquidtightly.

Another embodiment shown in FIGS. 9 and 10 is a modified example of the embodiment shown in FIG. 8, in which a retention ring part 816 protruding to the radial outward direction is provided by integral molding on an injection needle connecting part 811 of a drug container 810 over the entire circumference thereof at a base end side with respect to the male screw forming part. Furthermore, a remaining part 823f is consecutively provided through a breaking part 823e on a connecting part 823b of a penetrating member 823 at a base end side with respect to the female screw forming part. The breaking part 823e is a narrow and thin member provided along the circumferential direction with constant intervals. A claw part 823g is provided as protruding from the remaining part 823f in the radial inward direction on a part or whole circumferential direction thereof, so as to engage (lock) a base end surface of the retention ring part 816. According to the configuration, in the case where the connector for communicating 820 and the drug solution container 810 are separated from each other, i.e., in the case where the screwing between the connecting part 823b of the penetrating member 823 and the injection needle connecting part 811 of the drug solution container 810 is released, the breaking part 823e is broken, and the remaining part 823f and the claw part 823g remain on the side of the injection needle connecting part 811. The base end surface of the claw part 823g is slanted to the tip end side in the radial inward direction. According to the configuration, upon connecting by screwing the connecting part 823b of the penetrating member 823 to the injection needle connecting part 811 of the drug solution container 810, the claw part 823g easily overstrides the retention ring part 816 from the tip end side to engage the base end surface thereof. Upon overstriding, the remaining part 823f, the claw part 823g and the like suffer elastic deformation in the radial outward direction.

Another embodiment shown in FIG. 11 is a modified example of the embodiment shown in FIGS. 9 and 10, in which a retention ring part 916 is formed separately from an injection needle connecting part 911 and is engaged with a circumferential groove 917 on an outside of the injection needle connecting part 911.

In another embodiment shown in FIG. 12, a retention ring part 1016 protruding in the radial outward direction is formed by integral molding on a base part of an injection needle connecting part 1011 of a drug solution container 1010 over the entire circumferential direction thereof. A claw part 1023g is provided as protruding from a base part 1023b of a penetrating member 1023 in the radial inward direction on a part or whole circumferential direction thereof, so as to engage releasably a base end surface of the retention ring part 1016. In this embodiment, upon separating the connector for communicating 1020 and the drug solution container 1010 from each other, such a mechanical force is applied that is to separate the connecting part 1023b of the penetrating member 1023 relatively from the injection needle connecting part 1011 of the drug solution container 1010, whereby the base part of the connecting part 1023b suffers elastic deformation in the radial outward direction to release the engagement of the claw part 1023g and the retention ring part 1016.

Another embodiment shown in FIG. 13 is a modified example of the embodiment shown in FIG. 12, in which a breaking part 1123e as a narrow and thin member and a remaining part 1123f are provided on a base part of a connecting part 1123b of a penetrating member 1123 in this order toward the base end side. A claw part 1123g is provided as protruding from the remaining part 1123f in the radial inward direction on a part or while circumferential direction thereof, so as to engage a base end surface of a retention ring part 1116. In this embodiment, upon separating the connector for communicating 1120 and the drug solution container 1110 from each other, such a mechanical force is applied that is to separate the connecting part 1123b of the penetrating member 1123 relatively from the injection needle connecting part 1111 of the drug solution container 1110, whereby the breaking part 1123e is broken, and the remaining part 1123f and the claw part 1123g remain on the side of the injection needle connecting part 1111.

Another embodiment shown in FIG. 14 is a modified example of the embodiment shown in FIG. 13, in which a retention ring part 1216 is formed separately from an injection needle connecting part 1211 and is engaged with a circumferential groove 1217 on an outside of the injection needle connecting part 1211.

Another embodiment shown in FIG. 15 is a modified example of the embodiment shown in FIG. 7, in which a male screw on an outside of a cylindrical wall 1315 is screwed in a female screw on an inside of a connecting part 1323b. The height of the cylindrical wall 1315 is set considerably lower than an injection needle connecting part 1311, and a ring-shaped fitting part 1323h formed on the connecting part 1323b is engaged therebetween. Furthermore, a seal material 1330 is engaged with a circumferential groove 1323i between the connecting part 1323b and the fitting part 1323h, and the seal material 1330 is in contact with a tip end of the cylindrical wall 1315, whereby the connecting part 1323b is liquidtightly connected to the injection needle connecting part 1311.

A preferred embodiment of the drug solution container with a connector for communicating according to the invention is a syringe-type drug solution container having a drug solution having been charged therein, i.e., a so-called prefilled syringe P, as shown in FIG. 16. In this case, a penetrating needle of the connector for communicating is sealed liquidtightly or airtightly with a cap 60 formed with butyl rubber or a thermoplastic elastomer, as shown in FIG. 1.

Next, the use of the drug solution container according to the invention will be described with reference to FIGS. 16 and 17. The drug solution container shown in FIG. 16 is substantially the same as that shown in FIG. 1.

First, a preferred embodiment of the drug solution container of the invention, i.e., a prefilled syringe P having a connector for communicating 20 connected liquidtightly and removably through a fragile portion 50 and a drug solution D1 (a resolvent in this case) having been charged therein, and a vial V having a drug D2 charged therein are prepared. As shown in FIG. 16①, a plunger 40 is connected to a gasket 30 of the prefilled syringe P. The prefilled syringe is then moved in the direction of the arrow A to slide an opening V1 of the vial V along a guide part 21 of the connector for communicating 20, whereby a rubber plug V2 of the vial V is penetrated with a penetrating needle 23a as shown in FIG. 16②. Thereafter, the plunger 40 is pushed in the direction of the arrow B, and thus, the drug solution D1 housed in the prefilled syringe P is injected into the vial V. The drug solution D1 and the drug D2 are mixed by well shaking the prefilled syringe P and the vial V in this configuration, so as to make a drug solution MD. The positions of the prefilled syringe P and the vial V are vertically reversed (inverted), and then the plunger 40 is pulled in the direction of the arrow (C) to aspirate the drug solution MD into the prefilled syringe P, as shown in FIG. 16③. Thereafter, as shown in FIG. 17④, the connector for communicating 20 is rotated in the direction of the arrow (D), and thus, the connector for communicating 20 is removed from the prefilled syringe P accompanied with the fragile portion 50 as shown in FIG. 17⑤. Finally, as shown in FIG. 17⑥, an injection needle 70 is attached to an injection needle connecting part 11 at a tip end of the prefilled syringe P, and thus, the drug solution MD can be injected to a vein or the like of a patient.

As having been clarified by the foregoing descriptions, according to the invention, a connector for communicating and a drug solution container can be liquidtightly and removably connected to each other by an ordinary sterilizing process, and an operation for preparation of a drug solution can be easily carried out in a short period of time without causing injury of an operator or coring. Furthermore, an effort to separate a metallic needle and plastic members can be omitted since no metallic needle is used.

What is claimed is:

1. A drug solution container with a connector for communicating comprising a drug solution container having at a tip end thereof an injection needle connecting part, and a hollow connector for communicating attached to a tip end of the drug solution container; the connector for communicating comprising a cylindrical guide part with a bottom capable of being slidably attached to an opening of a vial, and a hollow penetrating member provided at a center of a bottom of the guide part to penetrate the bottom; the penetrating member comprising a penetrating needle at a tip end side with respect to the bottom, and a connecting part at a base end side with respect to the bottom; and the connecting part being fitted on an outside of the injection needle connecting part and being connected to the injection needle connecting part, wherein a remaining part is consecutively provided through a breaking part on a base part of the connecting part of the penetrating member, the remaining part is engaged with the injection needle connecting part, and the breaking part is configured to be broken upon a separation of the connecting part of the penetrating member from the injection needle connecting part.

2. A drug solution container as claim in claim 1, wherein the connecting part of the penetrating member and the injection needle connecting part are screwed together, the remaining part is consecutively provided through the breaking part on the connecting part of the penetrating member at a base end side with respect to a screw forming part, and the breaking part is configured to be broken when the connecting part of the penetrating member and injection needle connecting part are unscrewed to separate the connecting part of the penetrating member from injection needle connecting part.

3. A drug solution container as claimed in claim 1, wherein the remaining part is engaged with the injection needle connecting part to connect the connecting part of the penetrating member to the injection needle connecting part.

4. A drug solution container as claimed in claim 1, wherein a seal material intervenes between an inside of the connecting part of the penetrating member and a tip end of the injection needle connecting part.

5. A drug solution container as claimed in claim 1, wherein the drug solution container comprises a barrel with an open base end having an injection needle connecting part at a tip end thereof, and a gasket inserted from the open base end of the barrel liquidtightly and slidably into the barrel.

6. A drug solution container as claimed in claim 1, wherein the drug solution container comprises a bottle capable of being easily deformed by pressing, having an injection needle connecting part at a tip end thereof.

7. A drug solution container as claimed in claim 1, wherein the drug solution container has a drug solution having been charged therein.

* * * * *